(12) United States Patent
Russell et al.

(10) Patent No.: US 9,556,494 B2
(45) Date of Patent: Jan. 31, 2017

(54) METHODS FOR DIAGNOSING HUMAN IMMUNODEFICIENCY VIRUS INFECTIONS

(71) Applicants: Cornell University, Ithaca, NY (US); Liverpool School of Tropical Medicine, Liverpool (GB)

(72) Inventors: David G. Russell, Ithaca, NY (US); Henry Mwandumba, Liverpool (GB); Kondwani Jambo, Liverpool (GB)

(73) Assignees: Cornell University, Ithaca, NY (US); Liverpool School of Tropical Medicine, Liverpool (GB)

( * ) Notice: Subject to any disclaimer, the term of this patent is extended or adjusted under 35 U.S.C. 154(b) by 0 days.

(21) Appl. No.: 14/360,051

(22) PCT Filed: Nov. 21, 2012

(86) PCT No.: PCT/US2012/066244
§ 371 (c)(1),
(2) Date: May 22, 2014

(87) PCT Pub. No.: WO2013/078302
PCT Pub. Date: May 30, 2013

(65) Prior Publication Data
US 2014/0342934 A1 Nov. 20, 2014

Related U.S. Application Data

(60) Provisional application No. 61/563,216, filed on Nov. 23, 2011.

(51) Int. Cl.
*C12Q 1/70* (2006.01)
(52) U.S. Cl.
CPC ............... *C12Q 1/703* (2013.01); *C12Q 1/70* (2013.01)
(58) Field of Classification Search
None
See application file for complete search history.

(56) References Cited

U.S. PATENT DOCUMENTS

| | | |
|---|---|---|
| 5,866,331 A | 2/1999 | Singer et al. |
| 6,210,875 B1 | 4/2001 | Patterson et al. |
| 2001/0008760 A1 | 7/2001 | King et al. |
| 2002/0037498 A1 | 3/2002 | Hallowitz et al. |
| 2006/0178841 A1 | 8/2006 | Fernandez |
| 2008/0096191 A1 | 4/2008 | Kauppinen et al. |
| 2008/0108054 A1 | 5/2008 | Basu et al. |
| 2011/0287423 A1 | 11/2011 | Mahiet et al. |

FOREIGN PATENT DOCUMENTS

WO 2012092367 A1 7/2012

OTHER PUBLICATIONS

Gupta et al. Journal of Virology. Oct. 2002, vol. 76(19), pp. 9868-9876.
Plata et al. Aids Research and Human Retroviruses, Aug. 1990, vol. 6(8), pp. 979-986.
Smith et al., Quantitative Analysis of Mononuclear Cells Expressing Human Immunodeficiency Virus Type 1 RNA in Esophageal Mucosa. The Journal of Experimental Medicine. Oct. 1994, vol. 180, pp. 1541-1546.
Patterson et al., Detection of HIV-RNA-Positive Monocytes in Peripheral Blood of HIV-Positive Patients by Simultaneous Flow Cytometric Analysis of Intracellular HIV RNA and Cellular Immunophenotype. Cytometry Apr. 1998, vol. 31, pp. 265-274.
Borzi et al. A fluorescent in situ hybridization method in flow cytometry to detect HIV-1 specific RNA. Journal of Immunological Methods. Jun. 21, 1996, vol. 193, pp. 167-176.
Busch et al. Time course of detection of viral and serologic markers preceding human immunodeficiency virus type 1 seroconversion: implications for screening of blood and tissue donors, Transfusion, Feb. 1995 vol. 35(2), pp. 91-97.
Deichmann et al., Ultra-sensitive FISH is a useful tool for studying chronic HIV-1 infection, Jounral of Virological Methods, Apr. 1997, vol. 65(1), pp. 19-25.
Patterson et al., Detection of HIV-1 DNA and messenger RNA in Individual Cells by PDR-Driven in Situ Hybridization and Flow Cytometry, Science, May 14, 1993, vol. 260, pp. 976-979.
Douglas et al. Automated Quantitation of Cell-Mediated HIV Type 1 Infection of Human Syncytiotrophoblast Cells by Fluorescence in Situ Hybridization and Laser Scanning Cytometry, AIDS Research and Human Retroviruses, Apr. 2001, vol. 17(6), pp. 507-516.
Vyboh et al., Detection of viral RNA by fluorescence in situ hybridization (FISH), Journal of visualized experiments—JoVE May 2012, vol. 63, pp. e4002.
Lawrence et al., Subcellular localization of low-abundance human immunodeficiency virus nucleic acid sequences visualized by fluorescence in situ hybridization, Proc. Nati. Acad. Sci. USA vol. 87, pp. 5420-5424, Jul. 1990.
Somasundaran et al., Localization of HIV RNA in mitochondria of infected cells: potential role in cytopathogenicity, Journal of Cell Biology, Sep. 15, 1994, vol. 126(6), pp. 1353-1360.
Singer et al., Detection of HIV-1-infected cells from patients using nonisotopic in situ hybridization, Blood Nov. 1, 1989 74:6, pp. 2295-2301.
Knuchel et al., Incomplete HIV-1 Activation in Latently Infected U1 Cells Demonstrated by Double in Situ Hybridization, Virology, vol. 271, Issue 1, May 25, 2000, pp. 79-89.
Nakajima et al., In Situ Hybridization AT-Tailing with Catalyzed Signal Amplification for Sensitive and Specific in Situ Detection of Human Immunodeficiency Virus-1 mRNA in Formalin-Fixed and Paraffin-Embedded Tissues, Am. J. of Pathol., vol. 162:2, Feb. 2003, pp. 381-389.
Boe et al., Subcellular localization of human immunodeficiency virus type 1 RNAs, Rev, and the splicing factor SC-35, Virology, May 10, 1998, vol. 244(2), pp. 473-482.

(Continued)

*Primary Examiner* — Catherine S Hibbert
(74) *Attorney, Agent, or Firm* — Hodgson Russ LLP

(57) ABSTRACT

Provided is a method for identifying human immunodeficiency virus (HIV) in a sample. The invention involves use of a plurality of fluorescently labeled oligonucleotide probes and flow cytometry to detect the presence or absence of HIV in macrophages that are obtained from a mucosal surface. The invention is particularly useful for detecting HIV infection prior to seroconversion.

6 Claims, 4 Drawing Sheets

(56) References Cited

OTHER PUBLICATIONS

Wang et al., DNA electrochemical biosensor for the detection of short DNA sequences related to the human immunodeficiency virus, Anal. Chem. Aug. 1, 1996, vol. 68(15), pp. 2629-2634.

Yeh et al., Real-time molecular methods to detect infectious viruses, Seminars in Cell & Developmental Biology vol. 20, Feb. 4, 2009, pp. 49-54.

Meng et al., Automated Multiplex Assay System for Simultaneous Detection of Hepatitis B Virus DNA, Hepatitis C Virus RNA, and Human Immunodeficiency Virus Type 1 RNA, J Clin Microbiol. Aug. 2001; vol. 39(8): pp. 2937-2945.

Wu et al., Laboratory Testing on HIV and Research Progress, Chinese Journal of Frontier Health and Quarantine, Issue 4, vol. 32, Aug. 31, 2009, Abstract and Section 3.1.

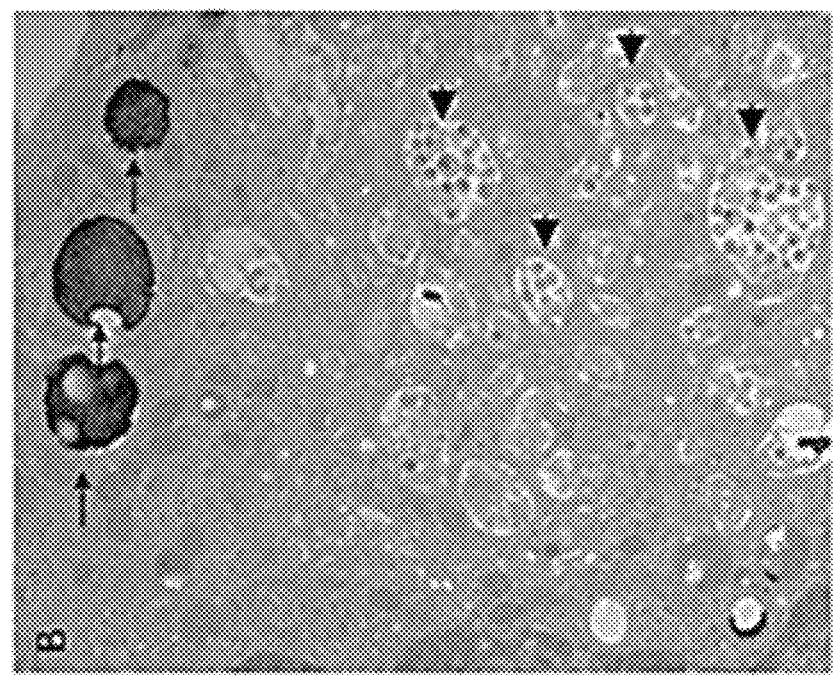
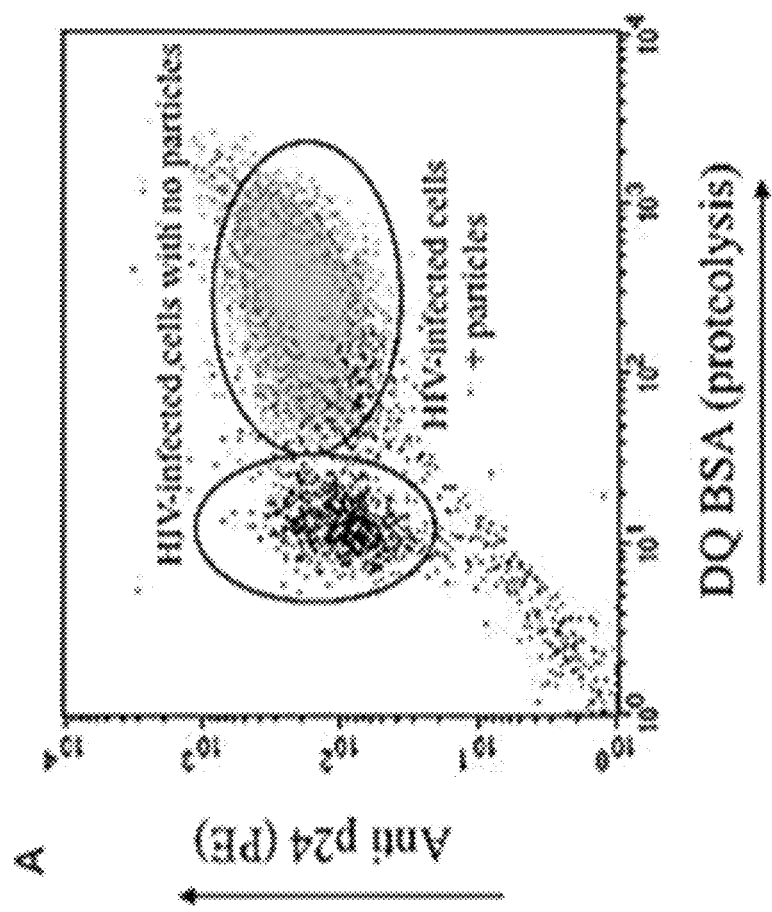
Figure 1

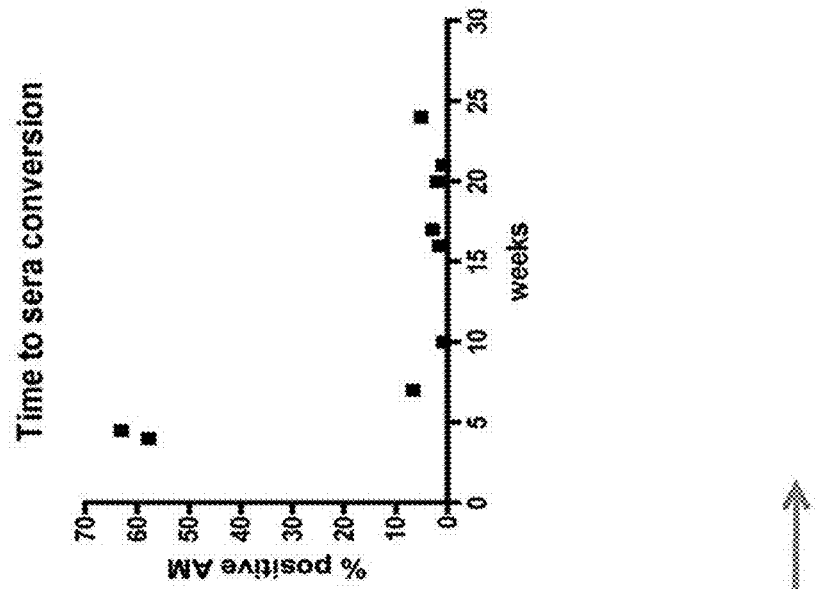
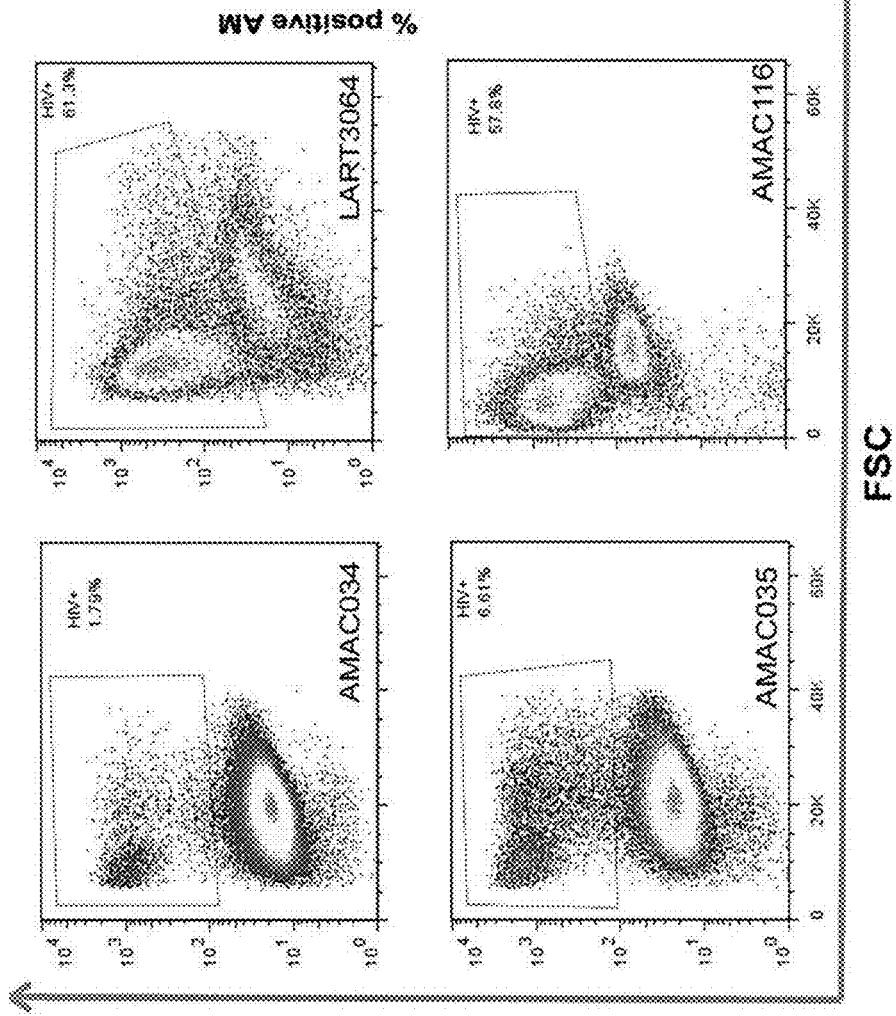

METHODS FOR DIAGNOSING HUMAN IMMUNODEFICIENCY VIRUS INFECTIONS

CROSS REFERENCE TO RELATED APPLICATIONS

This application claims priority to U.S. Provisional application No. 61/563,216, filed on Nov. 23, 2011, the disclosure of which is incorporated herein by reference.

STATEMENT REGARDING FEDERALLY SPONSORED RESEARCH

This invention was made with government support under contract no. HL100928 awarded by the National Institutes of Health. The government has certain rights in the invention.

FIELD OF THE INVENTION

The present invention relates generally to the detection and diagnosis of human immunodeficiency virus infection, and particularly to detection of human immunodeficiency (HIV) infection during early stages of the acute phase.

BACKGROUND OF THE INVENTION

Acute HIV (AHI) infection is the stage of infection prior to seroconversion and proper diagnosis of HIV infection at this stage has remained unresolved with serious implications to public health—AHI is associated with the highest rates of secondary HIV transmission over the course of infection.

Seroconversion has historically been believed to begin around 21 days after infection and to be complete in the majority of cases within 3 to 8 weeks of infection and represents the period during which a person with AHI would test negative by conventional means such as ELISA or Western Blot. And while AHI may be clinically diagnosed, the symptoms are nondescript and present in only half of infected individuals.

Elevated risk of HIV transmission during AHI results from the fact that AHI is characterized by the highest levels of viremia in an infected person prior to the onset of acquired immunodeficiency syndrome (AIDS), reaching their peak around 21 days post infection. This is then followed by a sharp decline due to the mounting immune response and seroconversion. In fact, there exists a strong positive correlation between viral load and rate of HIV transmission—each log increase in viral load is associated with an increase by a factor of 2.45 in the risk of transmission. Behavioral factors also contribute heavily to the elevated rate of HIV transmission during AHI-infected individuals during AHI are seldom aware of their infected status and are likely to sustain the activities that led to their infection, which puts the uninfected population at risk. Therefore, there exists a great need to be able to properly diagnose AHI. The present invention meets this need.

SUMMARY OF THE INVENTION

The present invention provides tools and methods for detecting HIV. The method is tailored for detecting HIV in macrophages obtained from a mucosal surface. In particular, the invention enables detecting HIV infection of macrophages before seroconversion in an individual. The method comprises providing a sample obtained from a mucosal surface, wherein the sample comprises macrophages. The macrophages are contacted with a plurality of fluorescently labeled oligonucleotide probes complementary to HIV mRNA. The probes each have a distinct sequence and are non-overlapping with respect to their complementarity to the target HIV mRNA. In certain embodiments, the plurality of probes is complementary to HIV Gag mRNA, or to HIV gp120 mRNA. In certain embodiments, the plurality of probes can comprise up to and including 48 probes.

Once the fluorescently labeled probes are introduced into macrophages, fluorescence in situ hybridization (FISH) is used in combination with flow cytometry to identify macrophages as infected with HIV based on a fluorescent signal emitted from the macrophages, or as not infected with HIV based on a lack of or a different fluorescent signal emitted from the macrophages. Based on a determination of HIV presence or absence in a sample, the individual from whom the sample was obtained can be diagnosed as HIV positive or HIV negative, respectively.

In general the method is used to determine HIV infection in a sample from an individual who has not seroconverted for anti-HIV antibodies. In certain aspects, the method involves determining HIV infection by separating a sample comprising macrophages from a mucosal surface, wherein at least some of the macrophages in the sample were infected in vivo within a certain time period before the sample is obtained and/or tested, such as within sixteen weeks to within one day of the infection.

The invention also provides kits comprising the plurality of probes that are useful in performing the method of the invention.

BRIEF DESCRIPTION OF THE FIGURES

FIG. 1A. PBMC-derived macrophages were infected with HIV and incubated for 6 days for the infection to establish. These macrophages were then fed DQ BSA beads and incubated for 180 minutes to facilitate proteolytic processing of the fluorescent reporter substrate. At that time the cells were harvested, fixed and labeled with PE-conjugated antibody against the HIV p24 protein. All samples were analyzed by FISH in combination with cell sorting and compared to unprocessed DQ BSA particles and to BSA particles that had been internalized for 180 minutes by control, uninfected PBMC-derived macrophages, which were also probed with anti-p25 antibodies and were determined to be HIV negative. FIG. 1B. Electron micrograph of the PBMCs fed IgG-coated latex beads (arrows) (120 minutes). The latex bead phagosomes do not intersect with the regions of the cells involved in viral budding (arrowheads). These regions can appear as small vesicles.

FIG. 3A. Graphical representation of FISH based flow cytometry analysis of the alveolar macrophages from HIV sera negative individuals with a positive reaction against a FISH probe set directed against HIV Gag mRNA. The number of positive macrophages varies greatly and up to 60% of the total macrophages. FIG. 3B. Graph showing the negative correlation between the % positive alveolar macrophages and the time to sera conversion for eight individuals who sera-converted after analysis of the alveolar macrophages using the method of the invention.

DETAILED DESCRIPTION OF THE INVENTION

Figure 2:
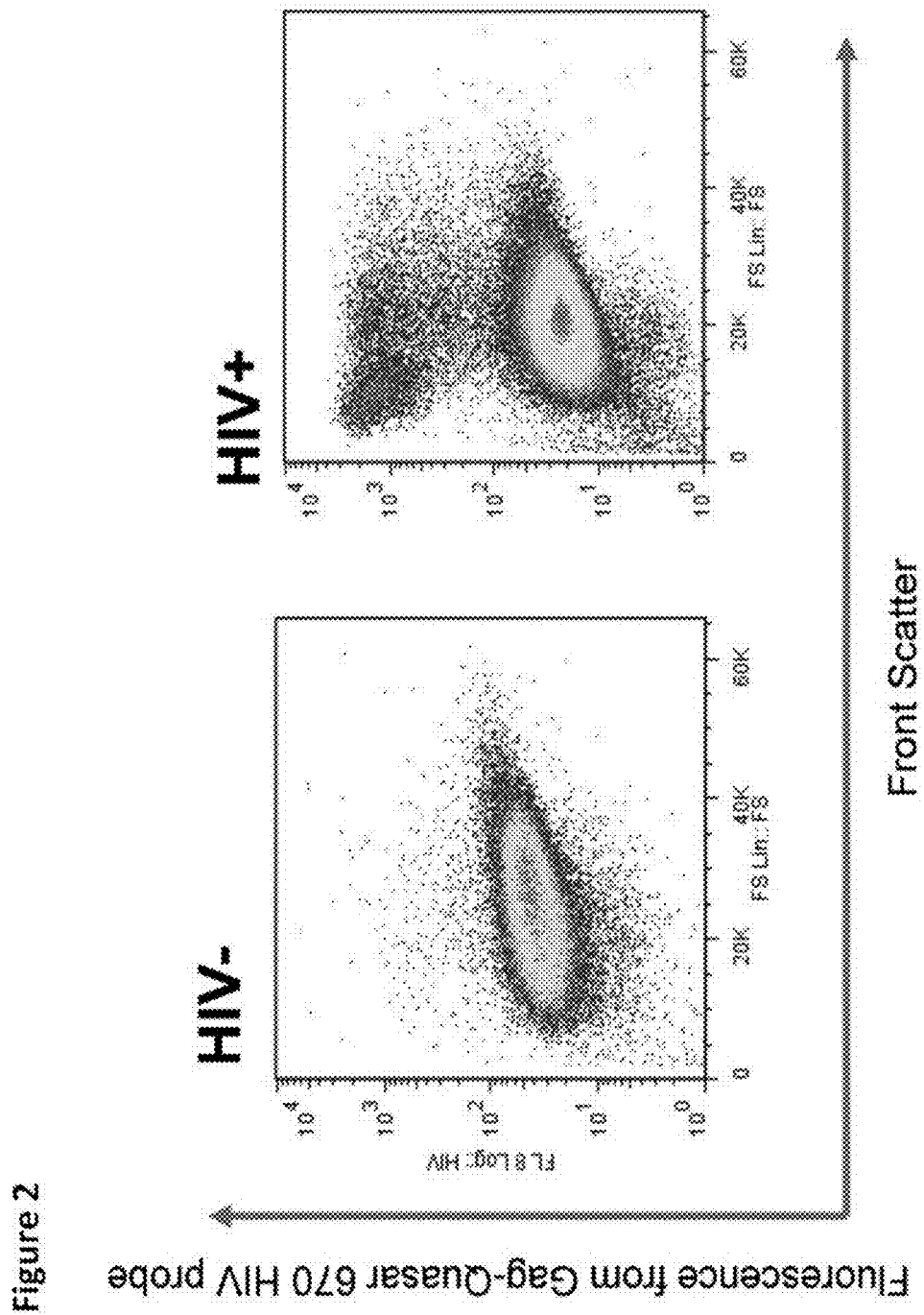
FIG. 2. Graphical representation of FISH based flow cytometry analysis of alveolar macrophages obtained from HIV seronegative (HIV−) and HIV seropositive (HIV+) individuals.

The present invention provides methods and compositions for determining HIV infection and is particularly suited for making this determination before seroconversion has taken place in an individual. Accordingly, in various embodiments the invention provides for diagnosis of AHI, and also includes determining the absence of AHI.

In various aspects, the invention facilitates determining whether or not macrophages are infected with HIV. Compositions and methods for determining HIV infection in macrophages at certain time points after HIV-infection are provided.

The invention is based in part on our surprising discovery of HIV infected alveolar macrophages in individuals who were HIV seronegative, and who were also negative for HIV infection as determined by several other tests, as will be further described below. In this regard, determining the sequence of early events following HIV infection is a challenging and critical area of research. Many studies indicate that there is an "eclipse" period of early infection during which virus is undetectable in the blood. However, the identity of the initial cell types infected, and the mechanism and site(s) of subsequent viral amplification remain to be elucidated. The more accepted viewpoint, reiterated repeatedly in reviews, is that following uptake across the mucosa by dendritic cells, the virus is delivered to CD4 cells. The resulting viral expansion leads to extensive depletion of mucosal lymphocytes, and the establishment of primary sites of infection at the lymph nodes. This is responsible for the peripheral expansion of the virus prior to the development of a limiting immune response. However, in contrast to the prevailing theory, the present invention demonstrates the expansion of HIV in the alveolar macrophages of HIV sera–ve individuals, who subsequently go on to sera convert to HIV sera+ve. These individuals lack detectable peripheral viremia, and their time to sera conversion in inversely proportional to the viral burden in their alveolar macrophages. These findings indicate an alternative scenario for viral amplification during acute stage infection and the invention takes advantage of this discovery to provide for improved HIV diagnosis.

In general, the invention involves using a plurality of oligonucleotide probes targeted to HIV mRNA to identify macrophages which have been infected by HIV. The probes comprise a detectable label that emits a fluorescent signal upon excitation with light having a particular wavelength. The probes are suitable for use in FISH analysis, whereby the fluorescent signals are determined using a flow cytometry procedure that is similar to fluorescence activated cell sorting (FACS) without the sorting step. The fluorescent signal can be used to characterize macrophages as either HIV positive or HIV negative. The present invention thus includes a combination of FISH and flow cytometry-based analysis of HIV infection.

The detectable labels attached to the probes can comprise any of a wide range of fluorophores, which are sometimes referred to in the art as "fluors." The detectable label as referred to herein is thus considered a "fluorescent label" and the oligonucleotide probes which include a fluorescent label are considered "fluorescently labeled."

Any fluorescent label that can be used in nucleic-acid based fluorescent microscopy imaging and/or in FISH, and/or in FISH/flow cytometry can be used to make fluorescently labeled probes for use in the invention. If desired, the FISH-based flow cytometry can include sorting cells into different containers. Suitable fluorescent labels are known in the art and are commercially available. Some non-limiting examples include, for instance, fluorescent dyes sold commercially under the trade name Quasar® as Quasar 570, Quasar 670 and Quasar 705, which have emission maxima at 570, 670 and 705 nm, respectively. Other suitable fluorescent labels include but are not limited to those sold under the trade name Alexa Fluor®, as well as Diethylaminocoumarin (DEAC), Cyanine 3 (Cy3), Cyanine 5 (Cy5), Fluorescein (FITC), Lissamine, R110, R6G, Tetramethylrhodamine (TAMRA), and Texas Red. In certain embodiments, the fluorescent marker fluoresces at 670 nm following excitation at 647 nm. In certain embodiments, the fluorescently labeled probes can be obtained commercially. For example, in an embodiment of the invention, fluorescently labeled probes sold under the trade name Stellaris® available from Biosearch Technologies, Inc., Novato Calif., are used in the invention.

The fluorescent label can be incorporated into the oligonucleotide probes using any suitable technique. In some non-limiting examples, the fluorescent label is chemically attached to a modified nucleotide to provide, for example, a fluorochrome-conjugated nucleotide that is present in the oligonucleotide probe.

In one aspect, the invention includes testing for HIV in a sample, wherein the sample comprises macrophages obtained from a mucosal surface. The mucosal surface can be any mucosal surface, including but not necessarily limited to alveolar mucosa, buccal mucosa, esophageal mucosa, gastric mucosa, intestinal mucosa, nasal mucosa, oral mucosa, bronchial mucosa, uterine mucosa, penile mucosa, vaginal mucosa, anal mucosa and endometrial mucosa. In one embodiment, a sample obtained from a mucosal surface includes a sample of mucous that is expelled by an individual via an oral or nasal route. Any suitable techniques for obtaining a sample of mucosa which comprises or is expected to comprise macrophages can be used. In certain embodiments, the sample can be obtained by swabbing, scraping, or biopsy of a mucosal surface. In one embodiment, the sample comprises alveolar mucosa. In certain approaches, the sample comprising alveolar mucosa is obtained by bronchoalveolar lavage.

The invention is expected to be useful for testing for any HIV type, group and subtype. In general the invention will be used to test for HIV-1, and typically for HIV-1 group M. It is expected that any of the nine presently known group M subtypes (or clades) A, B, C, D, F, G, H, J and K will be readily detected by performing the present invention by, which in certain embodiments may entail adapting the probe sequences to be complementary to any differences in the Gag and go120 genes present in these subtypes.

Macrophages tested via the method of the invention can be identified by cell surface markers that are well known to those skilled in the art, such as CD14, CD40, CD11b, EMR1 (human), lysozyme M, MAC-1/MAC-3 and CD68. In certain embodiments, the sample tested does not include circulating cells, such as circulating monocytes. In certain embodiments, the sample does not include peripheral blood mononuclear cells (PBMCs). In certain embodiments, the only cell type analyzed in performing the method are macrophages.

Once a sample comprising macrophages is obtained it is contacted with a plurality of fluorescently labeled oligonucleotide probes having distinct sequences, wherein the probes are complementary to HIV mRNA. In certain embodiments, the probes are complementary to HIV Gag mRNA, or to HIV gp120 mRNA, or to combinations thereof. The sequences of these HIV mRNAs are well known in the art.

The invention utilizes pluralities of fluorescently labeled probes, which can be provided as one or more sets of probes. In various embodiments, the plurality of fluorescently labeled probes comprises a first set of probes, each first set probe comprising a sequence complementary to HIV Gag mRNA, or a second set of probes, each second set probe comprising a sequence complementary to HIV gp120 mRNA, or a combination of the first set and second set probes.

Each probe in each set of probes comprises or consists of a distinct, defined nucleotide sequence of known length. For instance, a first set of probes will contain a plurality of members, each of which is complementary to, for example, HIV Gag mRNA. Each of the probes comprises or consists of a distinct and non-overlapping sequence with respect to the other probes in the set, meaning the probes do not overlap the message sequence to which they are complementary. The entire nucleotide sequence of each probe can be complementary to the particular HIV mRNA sequence. Similarly, a second set of probes can be provided, wherein each of its members is complementary to an HIV mRNA different from HIV Gag mRNA, such as HIV gp120 mRNA. As with the first probe set, each of the probes in the second set comprises or consists of a distinct and non-overlapping sequence with respect to the other probes in the set.

Each probe set can comprise probes that are 7-40 nucleotides in length, inclusive, and including all integers there between, and including all ranges of integers there between. In various embodiments, the probes are 15-30 nucleotides in length. In one embodiment, the probes are 20 nucleotides in length. The probes may comprise modified nucleotides which can include, in addition to nucleotides modified to include a detectable label, modifications which improve the stability or binding affinity of the probes. Examples of such modifications and methods for making them are well known in the art. In addition, the nucleotides may be linked via bonds other than a phosphodiester. Examples of internucleoside linkages include but are not limited to palkylphosphonate, phosphorothioate, phosphorodithioate, phosphate ester, alkylphosphonothioate, phosphoramidate, carbamate, carbonate, morpholino, acetamidate, carboxymethyl ester, or combinations thereof.

The probes can be complementary to any HIV mRNA that is expressed or present in an infected macrophage during AHI. As discussed above, in particular embodiments, the probes are complementary to HIV Gag mRNA or to HIV gp120 mRNA.

The sets of probes can contain variable numbers of probes. In one embodiment, the set comprises at least 20 probes. In a particular embodiment, the set comprises from twenty-four probes to fifty probes. In an embodiment, the set includes at least one first probe set comprising 48 probes targeted to one HIV mRNA.

In one embodiment, a first probe set consists of 48 probes targeted to HIV Gag mRNA. In one embodiment, the 48 probes targeted to HIV Gag mRNA have the sequences of SEQ ID NO:1 SEQ ID NO:48 as shown in Table 1.

TABLE 1

| | |
|---|---|
| TCCCATCGATCTAATTCTCC | SEQ ID NO: 1 |
| TTAATACTGACGCTCTCGCA | SEQ ID NO: 2 |
| ATTTTTTCTTTCCCCCTGGC | SEQ ID NO: 3 |
| CTGCTTGCCCATACTATATG | SEQ ID NO: 4 |
| AACTGCGAATCGTTCTAGCT | SEQ ID NO: 5 |
| ATGTTTCTAACAGGCCAGGA | SEQ ID NO: 6 |
| CCAGTATTTGTCTACAGCCT | SEQ ID NO: 7 |
| TGTCTGAAGGGATGGTTGTA | SEQ ID NO: 8 |
| GAGGGTTGCTACTGTATTAT | SEQ ID NO: 9 |
| CTCTATCCTTTGATGCACAC | SEQ ID NO: 10 |
| AAGCTTCCTTGGTGTCTTTT | SEQ ID NO: 11 |
| TGCTCTTCCTCTATCTTGTC | SEQ ID NO: 12 |
| CTGCTTGCTGTGCTTTTTTC | SEQ ID NO: 13 |
| TTTTGGCTGACCTGATTGCT | SEQ ID NO: 14 |
| GATGTTCTGCACTATAGGGT | SEQ ID NO: 15 |
| ATGGCCTGATGTACCATTTG | SEQ ID NO: 16 |
| CTGAAAGCCTTCTCTTCTAC | SEQ ID NO: 17 |
| GCTGAAAACATGGGTATCAC | SEQ ID NO: 18 |
| TTAAATCTTGTGGGGTGGCT | SEQ ID NO: 19 |
| CCCACTGTGTTTAGCATGGT | SEQ ID NO: 20 |
| TTTGCATGGCTGCTTGATGT | SEQ ID NO: 21 |
| CTTCCTCATTGATGGTCTCT | SEQ ID NO: 22 |
| ATGCACTCTATCCCATTCTG | SEQ ID NO: 23 |
| TCATCTGGCCTGGTGCAATA | SEQ ID NO: 24 |
| TATGTCACTTCCCCTTGGTT | SEQ ID NO: 25 |
| GAAGGGTACTAGTAGTTCCT | SEQ ID NO: 27 |
| CTACTGGGATAGGTGGATTA | SEQ ID NO: 27 |
| CTGGTAGGGCTATACATTCT | SEQ ID NO: 28 |
| GTCCTTGTCTTATGTCCAGA | SEQ ID NO: 29 |
| CATAGTCTCTAAAGGGTTCC | SEQ ID NO: 30 |
| GCTCGGCTCTTAGAGTTTTA | SEQ ID NO: 31 |
| CAACAAGGTTTCTGTCATCC | SEQ ID NO: 32 |
| AATCTGGGTTCGCATTTTGG | SEQ ID NO: 33 |
| GCTGGTCCCAATGCTTTTAA | SEQ ID NO: 34 |
| CCTGACATGCTGTCATCATT | SEQ ID NO: 35 |
| AAAACTCTTGCCTTATGGCC | SEQ ID NO: 36 |
| TACTTGGCTCATTGCTTCAG | SEQ ID NO: 37 |
| CTGCATCATTATGGTAGCTG | SEQ ID NO: 38 |
| CTTTGGTTCCTAAAATTGCC | SEQ ID NO: 39 |
| CCCTTCTTTGCCACAATTGA | SEQ ID NO: 40 |

TABLE 1-continued

| | |
|---|---|
| TCCAACAGCCCTTTTTCCTA | SEQ ID NO: 41 |
| TTTGGTGTCCTTCCTTTCCA | SEQ ID NO. 42 |
| CCTGTCTCTCAGTACAATCT | SEQ ID NO: 43 |
| GGCCAGATCTTCCCTAAAAA | SEQ ID NO: 44 |
| AAGAAAATTCCCTGGCCTTC | SEQ ID NO: 45 |
| ACCTGAAGCTCTCTTCTGGT | SEQ ID NO: 46 |
| TACAGTTCCTTGTCTATCGG | SEQ ID NO: 47 |
| TGACCTGAGGGAAGTTAAAG | SEQ ID NO: 48 |

In another embodiment, a second probe set consists of 48 probes targeted to HIV gp120 mRNA. In one embodiment, the 48 probes targeted to HIV gp120 mRNA have the sequences of SEQ ID NO:49 SEQ ID NO:96 as shown in Table 2.

TABLE 2

| | |
|---|---|
| CCACAATTTTTCTGTAGCAC | SEQ ID NO: 49 |
| GTACCCCATAATAGACTGTG | SEQ ID NO: 50 |
| AATAGAGTGGTGGTTGCTTC | SEQ ID NO: 51 |
| TGCTTTAGCATCTGATGCAC | SEQ ID NO: 52 |
| GCCCAAACATTATGTACCTC | SEQ ID NO: 53 |
| TGTGGGTACACAGGCATGTG | SEQ ID NO: 54 |
| TACTACTTCTTGTGGGTTGG | SEQ ID NO: 55 |
| CCATGTCATTTTCCACATG | SEQ ID NO: 56 |
| ATATCCTCATGCATCTGTTC | SEQ ID NO: 57 |
| GGCTTTGATCCCATAAACTG | SEQ ID NO: 58 |
| CTAACACAGAGTGGGGTTAA | SEQ ID NO: 59 |
| CATTCTTCAAATCAGTGCAC | SEQ ID NO: 60 |
| CCCGCTACTACTATTGGTAT | SEQ ID NO: 61 |
| CTCTCCTTTCTCCATTATCA | SEQ ID NO: 62 |
| GCTGATATTGAAAGAGCAGT | SEQ ID NO: 63 |
| GCACCTTACCTCTTATGCTT | SEQ ID NO: 64 |
| GTCAACTTATAGCTGGTAGT | SEQ ID NO: 65 |
| CTGTGTAATGACTGAGGTGT | SEQ ID NO: 66 |
| CAAAGGATACCTTTGGACAG | SEQ ID NO: 67 |
| GGCACAATAATGTATGGGAA | SEQ ID NO: 68 |
| TTAGAATCGCAAAACCAGCC | SEQ ID NO: 69 |
| CCTGTTCCATTGAACGTCTT | SEQ ID NO: 70 |
| GTACATTGTACTGTGCTGAC | SEQ ID NO: 71 |
| GATACTACTGGCCTAATTCC | SEQ ID NO: 72 |
| GCCATTTAACAGCAGTTGAG | SEQ ID NO: 73 |
| CTACCTCTTCTTCTGCTAGA | SEQ ID NO: 74 |
| GTCCGTGAAATTGACAGATC | SEQ ID NO: 75 |

TABLE 2-continued

| | |
|---|---|
| CAGATGTGTTCAGCTGTACT | SEQ ID NO: 76 |
| GTTGTTGGGTCTTGTACAAT | SEQ ID NO: 77 |
| CTCTCTGGATACGGATTCTT | SEQ ID NO: 78 |
| TGTAACAAATGCTCTCCCTG | SEQ ID NO: 79 |
| GTGCTTGTCTCATATTTCCT | SEQ ID NO: 80 |
| CCATTTTGCTCTACTAATGT | SEQ ID NO: 81 |
| GCTAGCTATCTGTTTTAAAG | SEQ ID NO: 82 |
| CTCCTGAGGATTGCTTAAAG | SEQ ID NO: 83 |
| TGCGTTACAATTTCTGGGTC | SEQ ID NO: 84 |
| GTAGAAAAATTCCCCTCCAC | SEQ ID NO: 85 |
| CCTTCAGTACTCCAAGTACT | SEQ ID NO: 86 |
| GTGTCACTTCCTTCAGTGTT | SEQ ID NO: 87 |
| TTTATTCTGCATGGGAGGGT | SEQ ID NO: 88 |
| CCTACTTTCTGCCACATGTT | SEQ ID NO: 89 |
| AATTTGTCCACTGATGGGAG | SEQ ID NO: 90 |
| CAGCCCTGTAATATTTGATG | SEQ ID NO: 91 |
| GCTATTACCACCATCTCTTG | SEQ ID NO: 92 |
| TGAAGATCTCGGACTCATTG | SEQ ID NO: 93 |
| ATTGTCCCTCATATCTCCTC | SEQ ID NO: 94 |
| GTGCTACTCCTAATGGTTCA | SEQ ID NO: 95 |
| ACTCTTCTCTTTGCCTTGGT | SEQ ID NO: 96 |

In various embodiments, the method involves using fluorescently labeled probes which comprise or consist of the sequences set forth in Table 1, or fluorescently labeled probes which comprise or consist of the sequences set forth in Table 1, or combinations of the probes in Table 1 and Table 2. The invention includes using all combinations and sub-combinations of Table 1 probes, Table 2 probes, and mixtures of Table 1 and Table 2 probes. In certain embodiments, the only probes used in the invention are a combination of probes from Table 1, (wherein included in such combinations is the combination of all of the probes in Table 1), or a combination of probes from Table 2, (wherein included in such combinations is the combination of all of the probes in Table 2).

In general, well known techniques can be used to introduce the fluorescently labeled probes of the invention into macrophages in a sample to be tested for HIV. These techniques typically involve permeabilizing the cells and incubating the cells with a combination of the probes in a solution, such as a buffer and allowing a period of time for probe hybridization, after which excess/unbound probes are removed. Thus, in one embodiment, the invention provides for making a composition comprising isolated macrophages, wherein the macrophages are obtained from a mucosal surface, and wherein the macrophages comprise a set of probes complementary to HIV mRNA. In certain embodiments the composition comprises macrophages which in turn comprise the plurality of probes hybridized to HIV mRNA. In certain embodiments, the macrophages were infected with HIV within a certain time period of the introduction of the probes. In certain embodiments, the method of the invention is carried out within a certain time period after obtaining a sample from an HIV seronegative individual.

Once the probes are introduced into the macrophages, the macrophages are tested using a flow cytometry apparatus. Any of a variety of flow cytometry apparatuses are commercially available and can be used for testing a sample according to the invention. In general, the flow cytometer is adapted for exposing individual cells to light of a particular excitation wavelength, and for detecting resulting fluorescence of a particular wavelength that is emitted from the macrophages due to excitation of the fluor attached to the probes. The presence or absence of fluorescence, as well as the degree of fluorescence, can be determined and quantified so that HIV positive and HIV negative cells can be separately identified and if desired the individual cells of each type (infected and non-infected) can be counted. Further, the ratio, percentage, etc. of HIV positive to HIV negative cells can be determined and used to, for example, assess the stage or severity of HIV infection in an individual from which the macrophages were obtained. If desired, HIV positive and HIV negative cells can be sorted into separate containers, thereby converting the FISH based flow cytometry process to a FACS process.

In certain embodiments, macrophages that are analyzed by flow cytometry according to the invention can also be characterized by macrophage markers, such as cell surface markers that are indicative of the macrophage cell type. For example, the macrophages can be identified during the flow cytometry analysis using detectably labeled antibodies directed to macrophage CD45, CD206, HLA-DR, or combinations thereof. The detectable label can be a fluorescent label of the type described above, and a fluorescent signal from the antibodies can be detected during flow cytometry analysis in the same way as can a fluorescent signal from the fluorescently labeled oligonucleotide probes. In this regard, our phenotypic characterization of HIV-infected alveolar macrophages confirmed their identity and indicated that they are poor expressors of HLA-DR (CD74) and the mannose receptor (CD206. Similar re-alignment of expression of HLA-DR and CD206 was seen in HIV-infected AM from chronic HIV+ve individuals, where we also observed constant levels of CD45 expression indicating that there was some measure of selectivity in the down-regulation of expression of surface proteins.

In one embodiment, the sample comprising macrophages that is analyzed according to the method of the invention is obtained from an HIV seronegative individual. Seronegativity for HIV is well known in the art and is generally considered to be the absence of detectable anti-HIV antibodies in a biological sample obtained from an individual. Seronegative individuals can therefore be not infected by HIV, or can be infected with HIV but have not yet developed detectable antibodies to one or more HIV proteins. In various embodiments, a biological sample obtained from a seronegative individual has no detectable antibodies to HIV proteins gp160, gp120, p65, p55, gp41, p32, p24 or p18, or combinations thereof. In one embodiment, a seronegative individual has no detectable anti-HIV antibodies as determined by Enzyme-linked immunosorbent assay (ELISA), including but not necessarily limited to an ELISA sandwich assay. In another embodiment, the sample comprising macrophages that is analyzed according to the method of the invention is obtained from a mucosal surface in an individual who has no detectable HIV in a blood sample, or a sample of PBMCs, as determined by use of PCR with PCR primers targeted to HIV mRNA, or to integrated HIV provirus. In each example of a seronegative individual, the invention includes testing macrophages which are infected with HIV.

In arriving at the present invention, we tested some individuals multiple times for seroconversion, yet still took up to 38 weeks to convert to sera+ve for HIV. Our data reveal a previously unappreciated degree of heterogeneity and delay in emergence from the "eclipse" phase of infection. We also recorded the CD4/CD8 ratio of all individuals during the process of sera conversion and observed the classic expansion of CD8 cells prior to the development of humoral immunity. We demonstrated that at the time leading up to sera conversion, the inversion of the CD8:CD4 ratio was due to both the expansion of the CD8+ T cell population and a reduction in CD4+ cell numbers. The rapid reduction in CD4+ cells is observed more closely linked to the acquisition of sera-positivity. Thus, because macrophages represent a long-lived source of infectious virus, the present invention provides an important new contribution to detection of HIV infection.

In various embodiments, the invention provides for testing a sample comprising macrophages that are infected in vivo with HIV within a certain period of time before the test is performed. For example, the macrophages that were infected in vivo and obtained from a mucosal surface can be tested within 24 hours, or from one day to thirty eight weeks after infection, including each interval of days there between, or a longer period, provided the individual from which the macrophages were obtained was HIV seronegative. In one embodiment, the individual has been seronegative for at least 16 weeks after being infected by HIV. In general, the macrophages should be tested within hours or within several days after they are obtained from the individual. in certain embodiments, the cells can be stored for a period of at least two weeks in either a solution comprising paraformaldehyde or ethanol, such as 70% ethanol, with reduced temperature if desired.

In one embodiment, the invention is useful for predicting the time to seroconversion for an individual. In this regard, we have discovered that there is an inverse correlation between the percentage of HIV+ macrophages in the sample obtained from a mucosal surface and the time remaining to seroconversion. Stated differently, the higher the percentage of HIV+ macrophages as compared to total macrophages in the sample, the more proximate the seroconversion event is likely to be. Thus, in various aspects, the invention can include determining a percentage of HIV+ macrophages in a sample of macrophages and, optionally, developing a prognosis and/or treatment protocol for an individual based on this determination. For instance, by using sequential testing to determine changes in percentage of HIV+ mucosal macrophages over a period of time, the efficacy of an anti-retroviral therapy can be evaluated. Observing an increase in percentage of HIV+ mucosal macrophages permits recommending and/or implementing a change in the type, amount and/or dosing schedule of the anti-retroviral therapy. In certain embodiments, the invention also includes, subsequent to determination of the presence of HIV+ mucosal macrophages in a sample, administering to the individual from which the sample was obtained an anti-retroviral therapeutic agent.

In certain other aspects of the invention, kits for use in identifying HIV+ mucosal macrophages are also provided. The kits can provide any combination of fluorescently labeled oligonucleotide probes as described herein. The kits can accordingly comprise any or all of the probes described in Table 1, Table 2, or combinations thereof. The probes can be provided in one or more sealed, sterile vials. The kits can also comprise reagents, containers and the like for introducing the probes into macrophages obtained from a mucosal surface. The kits may further comprise materials and instructions for obtaining a sample comprising macrophages from a mucosal surface in an individual and for preparing the macrophages for analysis in the method of the invention.

The following specific examples are provided to illustrate the invention, but are not intended to be limiting in any way.

Example 1

As shown in FIG. 1, in in vitro infections of human monocyte-derived macrophages with HIV (BaL strain), the infection was easily detected by FISH and flow cyometry staining with anti-p24 antibody. The level of the infection was also visualized by electron microscopy. However, when human alveolar macrophages from HIV positive (HIV+ve) patients were probed with anti-p24 antibodies, the level of viral antigen was below the level of detection by flow cytometry. To enhance the signal a cocktail of antibodies against p24, p17, p120 and Gag was used. But again there was no detectable HIV in cells from HIV+ve patients. These results demonstrated that the viral burden in vivo is considerably lower than that found in vitro.

Example 2

Because of the lack of positive results described in Example 1, we revised our approach to investigate FISH as a technique to improve sensitivity of HIV detection. We engaged in this approach because of published reports that describe using this method successfully to detect HIV in lymphocytes from HIV-infected patients. We first attempted to use a commercially available flow cytometry based in situ HIV-1 mRNA test for intact human cells. The test is offered commercially with the characterization that it can be used in any single cell suspension appropriate for flow cytometry or image analysis, and that it is suitable for use with cell lines, peripheral blood, dissociated tissues, and bodily fluids. It also purports to be able to detect the presence of persistent HIV-1 replication in individuals with undetectable plasma viral load. However, our testing with this commercially available test failed to detect virus in either patients' cells or in 8Ef cells infected with a pseudovirus that lacked the Gag and Pol genes. We then used this pseudo virus as a template to generate single stranded DNA probes with primers that mapped to several sites on the viral chromosome. Again we were unsuccessful with the detection of virus in either patients' cells or cells infected in culture.

Example 3

In order to continue attempting to develop a test with previously unavailable sensitivity we utilized two different sets of fluorescently labeled probes having the sequences presented in Table 1 and Table 2, which we had prepared by Biosearch Technologies, Inc., (Novato, Calif.). We successfully probed for the presence of HIV in human alveolar macrophages from HIV+ve patient samples using the labeled probes using flow cytometry.

Example 4

Figure 4:
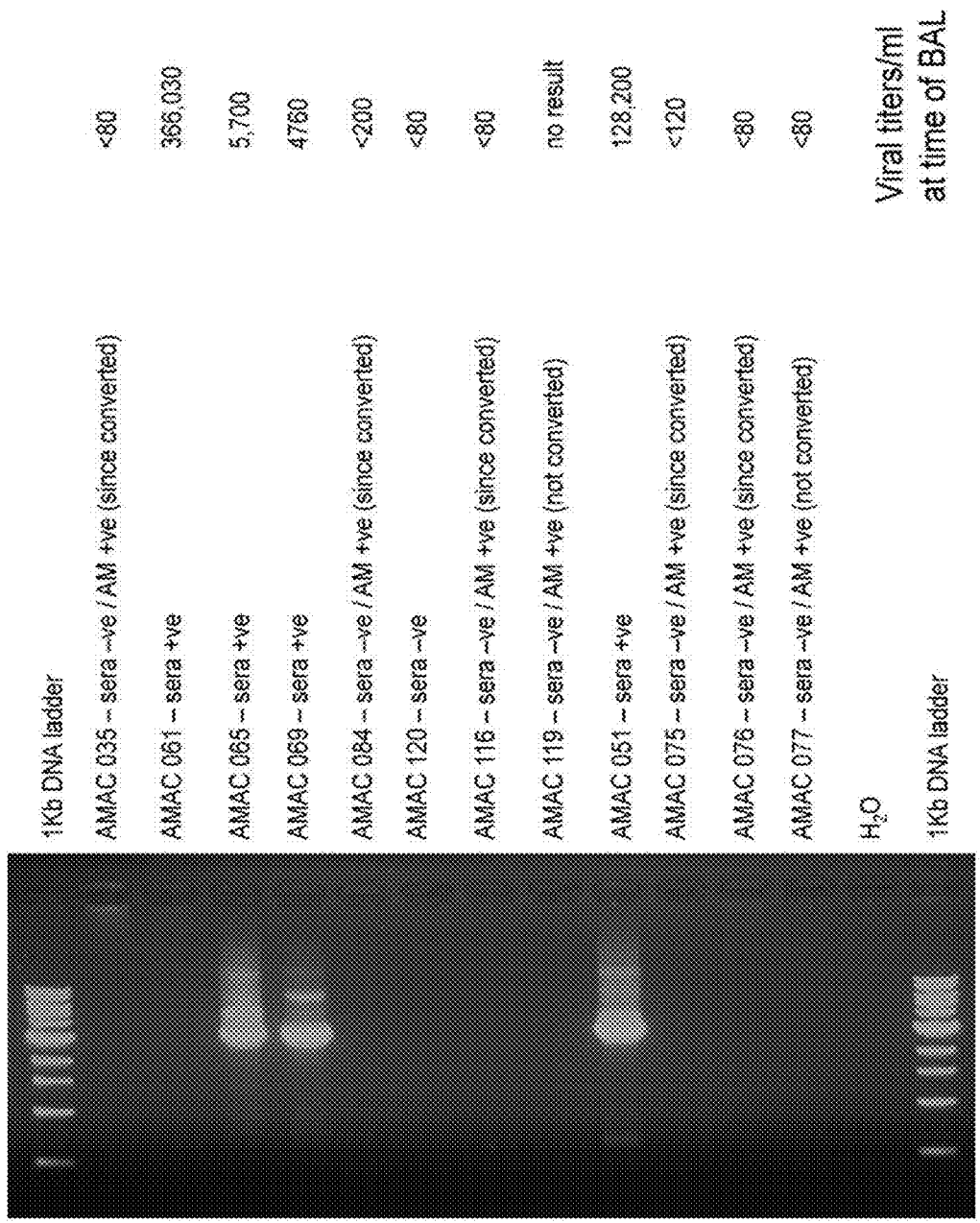
FIG. 4. Photographic representation of electrophoretically separated polymerase chain reaction (PCR) amplicons of the env gene from plasma samples from five individuals whose alveolar macrophages were HIV+ve, yet were sera−ve but subsequently seroconverted, two individuals whose AM were HIV+ve but had not sero-converted, three chronically HIV-infected individuals, and two individuals not infected with HIV.

The studies described above and additional work in chronically-infected, HIV sera+ve individuals demonstrated that we could successfully probe the functional status of HIV infected alveolar macrophages (AM) to compare with the uninfected AM in the same individual (compare "HIV−" to "HIV+" panels as shown in FIG. 2). However, we then unexpectedly and very surprisingly detected abundant virus in AM obtained from two HIV− (HIV sera−ve) individuals who we initially intended to serve as negative controls. Since this discovery we have used the method of the invention to detect HIV in ten HIV sera−ve individuals who, most significantly, have subsequently gone on to convert to sera+ve for HIV. The viral burden with respect to the number of infected cells in these individuals was very heterogeneous, ranging from a few percent up to 60% of the AM (FIG. 3A). It is significant to note that the time between detection of virus in the AM by using our combined fluorescent probe/flow cytometry approach and sera conversion to HIV+ve varied inversely with the % of infected macrophages (see FIG. 3B). This suggests strongly that viral amplification within myeloid cells is very significant for viral expansion during early infection. In support of this we analyzed the abundance of viral genomes in the plasma, and attempted to PCR amplify the env gene from plasma samples derived from 5 individuals whose AM were HIV+ve, yet were sera−ve but have since sero-converted, 2 individuals whose AM were HIV+ve but have not sero-converted, 3 chronically HIV-infected individuals and 2 individuals negative for HIV by all tests, (see FIG. 4). The env gene could only be amplified in those chronically-infected individuals, and the peripheral viral burden was uniformly low to undetectable in all other groups. This indicates that there is minimal viral expansion in the circulation during this early phase of infection and that detection of virus in the periphery at this time presents serious challenges. To date, we have tested samples from 17 individuals who are HIV-sera ve, yet show viral signal by FISH in their alveolar macrophages. The level of viral infection varied tremendously from around 1-2% up to over 60% of the AM. Of these 17 individuals, 8 subsequently sera-converted to HIV+ve. Time to seroconversion occurred in some individuals separately at approximately 6, 8, 10, 12 and 17 weeks after the initial detection of HIV in alveolar macrophages.

Thus, the present invention provides a surprisingly superior method for detecting early HIV infection, especially for the AHI phase prior to seroconversion.

To our knowledge this is the first time that fluorescence based flow cytometry has been used to detect HIV in macrophages of patients prior to seroconversion. Further, we have detected HIV at the individual cell (alveolar macrophage) level during acute HIV infection. Further still, we demonstrate that HIV infection is restricted to macrophages during the early acute infection phase, and that this is the reservoir that should be tested to identify AHI.

While the invention has been described through specific embodiments, routine modifications will be apparent to those skilled in the art and such modifications are intended to be within the scope of the present invention.

What is claimed is:

1. A method for detecting human immunodeficiency virus (HIV) in a sample comprising:
   i) providing a sample obtained from a mucosal surface present in the lungs of an individual, wherein the sample comprises macrophages;
   ii) contacting the sample with a plurality of fluorescently labeled oligonucleotide probes having distinct sequences, wherein the probes are complementary to HIV mRNA; and
   iii) using fluorescence in situ hybridization in combination with flow cytometry to identify macrophages as infected with HIV based on a fluorescent signal emitted from the macrophages or as not infected with HIV based on a lack of a fluorescent signal emitted from the macrophages,
   wherein the plurality of fluorescently labeled oligonucleotide probes comprises 48 distinct, non-overlapping probes that are each 20-30 nucleotides in length and are complementary to HIV gp120 mRNA.

2. The method of claim 1, wherein macrophages infected with HIV are identified, and wherein the macrophages were infected in vivo by HIV not more than eight weeks before performing step ii) and step iii).

3. The method of claim 2, wherein the macrophages were infected in vivo not more than four weeks before performing step ii) and step iii).

4. The method of claim 3, wherein the macrophages were infected in vivo not more than one week before performing steps ii) and steps iii).

5. The method of claim 1, wherein the macrophages are identified as not infected with HIV.

6. The method of claim 1, wherein the mucosal surface is present in an HIV seronegative individual.

* * * * *

SEQUENCE LISTING

<160> NUMBER OF SEQ ID NOS: 96

<210> SEQ ID NO 1
<211> LENGTH: 20
<212> TYPE: DNA
<213> ORGANISM: HIV

<400> SEQUENCE: 1
tcccatcgat ctaattctcc                                              20

<210> SEQ ID NO 2
<211> LENGTH: 20
<212> TYPE: DNA
<213> ORGANISM: HIV

<400> SEQUENCE: 2
ttaatactga cgctctcgca                                              20

<210> SEQ ID NO 3
<211> LENGTH: 20
<212> TYPE: DNA
<213> ORGANISM: HIV

<400> SEQUENCE: 3
attttttctt tccccctggc                                              20

<210> SEQ ID NO 4
<211> LENGTH: 20
<212> TYPE: DNA
<213> ORGANISM: HIV

<400> SEQUENCE: 4
ctgcttgccc atactatatg                                              20

<210> SEQ ID NO 5
<211> LENGTH: 20
<212> TYPE: DNA
<213> ORGANISM: HIV

<400> SEQUENCE: 5
aactgcgaat cgttctagct                                              20

<210> SEQ ID NO 6
<211> LENGTH: 20
<212> TYPE: DNA
<213> ORGANISM: HIV

<400> SEQUENCE: 6
atgtttctaa caggccagga                                              20

<210> SEQ ID NO 7
<211> LENGTH: 20
<212> TYPE: DNA
<213> ORGANISM: HIV

<400> SEQUENCE: 7
ccagtatttg tctacagcct                                              20

<210> SEQ ID NO 8
<211> LENGTH: 20
<212> TYPE: DNA
<213> ORGANISM: HIV

<400> SEQUENCE: 8

-continued tgtctgaagg gatggttgta                                              20

<210> SEQ ID NO 9
<211> LENGTH: 20
<212> TYPE: DNA
<213> ORGANISM: HIV

<400> SEQUENCE: 9
gagggttgct actgtattat                                              20

<210> SEQ ID NO 10
<211> LENGTH: 20
<212> TYPE: DNA
<213> ORGANISM: HIV

<400> SEQUENCE: 10
ctctatcctt tgatgcacac                                              20

<210> SEQ ID NO 11
<211> LENGTH: 20
<212> TYPE: DNA
<213> ORGANISM: HIV

<400> SEQUENCE: 11
aagcttcctt ggtgtctttt                                              20

<210> SEQ ID NO 12
<211> LENGTH: 20
<212> TYPE: DNA
<213> ORGANISM: HIV

<400> SEQUENCE: 12
tgctcttcct ctatcttgtc                                              20

<210> SEQ ID NO 13
<211> LENGTH: 20
<212> TYPE: DNA
<213> ORGANISM: HIV

<400> SEQUENCE: 13
ctgcttgctg tgctttttc                                               20

<210> SEQ ID NO 14
<211> LENGTH: 20
<212> TYPE: DNA
<213> ORGANISM: HIV

<400> SEQUENCE: 14
ttttggctga cctgattgct                                              20

<210> SEQ ID NO 15
<211> LENGTH: 20
<212> TYPE: DNA
<213> ORGANISM: HIV

<400> SEQUENCE: 15
gatgttctgc actatagggt                                              20

<210> SEQ ID NO 16
<211> LENGTH: 20
<212> TYPE: DNA
<213> ORGANISM: HIV

<400> SEQUENCE: 16
atggcctgat gtaccatttg                                           20

<210> SEQ ID NO 17
<211> LENGTH: 20
<212> TYPE: DNA
<213> ORGANISM: HIV

<400> SEQUENCE: 17
ctgaaagcct tctcttctac                                           20

<210> SEQ ID NO 18
<211> LENGTH: 20
<212> TYPE: DNA
<213> ORGANISM: HIV

<400> SEQUENCE: 18
gctgaaaaca tgggtatcac                                           20

<210> SEQ ID NO 19
<211> LENGTH: 20
<212> TYPE: DNA
<213> ORGANISM: HIV

<400> SEQUENCE: 19
ttaaatcttg tggggtggct                                           20

<210> SEQ ID NO 20
<211> LENGTH: 20
<212> TYPE: DNA
<213> ORGANISM: HIV

<400> SEQUENCE: 20
cccactgtgt ttagcatggt                                           20

<210> SEQ ID NO 21
<211> LENGTH: 20
<212> TYPE: DNA
<213> ORGANISM: HIV

<400> SEQUENCE: 21
tttgcatggc tgcttgatgt                                           20

<210> SEQ ID NO 22
<211> LENGTH: 20
<212> TYPE: DNA
<213> ORGANISM: HIV

<400> SEQUENCE: 22
cttcctcatt gatggtctct                                           20

<210> SEQ ID NO 23
<211> LENGTH: 20
<212> TYPE: DNA
<213> ORGANISM: HIV

<400> SEQUENCE: 23
atgcactcta tcccattctg                                           20

<210> SEQ ID NO 24
<211> LENGTH: 20
<212> TYPE: DNA
<213> ORGANISM: HIV

-continued

<400> SEQUENCE: 24
tcatctggcc tggtgcaata                                                   20

<210> SEQ ID NO 25
<211> LENGTH: 20
<212> TYPE: DNA
<213> ORGANISM: HIV

<400> SEQUENCE: 25
tatgtcactt ccccttggtt                                                   20

<210> SEQ ID NO 26
<211> LENGTH: 20
<212> TYPE: DNA
<213> ORGANISM: HIV

<400> SEQUENCE: 26
gaagggtact agtagttcct                                                   20

<210> SEQ ID NO 27
<211> LENGTH: 20
<212> TYPE: DNA
<213> ORGANISM: HIV

<400> SEQUENCE: 27
ctactgggat aggtggatta                                                   20

<210> SEQ ID NO 28
<211> LENGTH: 20
<212> TYPE: DNA
<213> ORGANISM: HIV

<400> SEQUENCE: 28
ctggtagggc tatacattct                                                   20

<210> SEQ ID NO 29
<211> LENGTH: 20
<212> TYPE: DNA
<213> ORGANISM: HIV

<400> SEQUENCE: 29
gtccttgtct tatgtccaga                                                   20

<210> SEQ ID NO 30
<211> LENGTH: 20
<212> TYPE: DNA
<213> ORGANISM: HIV

<400> SEQUENCE: 30
catagtctct aaagggttcc                                                   20

<210> SEQ ID NO 31
<211> LENGTH: 20
<212> TYPE: DNA
<213> ORGANISM: HIV

<400> SEQUENCE: 31
gctcggctct tagagtttta                                                   20

<210> SEQ ID NO 32
<211> LENGTH: 20
<212> TYPE: DNA

```
<213> ORGANISM: HIV

<400> SEQUENCE: 32
caacaaggtt tctgtcatcc                                              20

<210> SEQ ID NO 33
<211> LENGTH: 20
<212> TYPE: DNA
<213> ORGANISM: HIV

<400> SEQUENCE: 33
aatctgggtt cgcattttgg                                              20

<210> SEQ ID NO 34
<211> LENGTH: 20
<212> TYPE: DNA
<213> ORGANISM: HIV

<400> SEQUENCE: 34
gctggtccca atgcttttaa                                              20

<210> SEQ ID NO 35
<211> LENGTH: 20
<212> TYPE: DNA
<213> ORGANISM: HIV

<400> SEQUENCE: 35
cctgacatgc tgtcatcatt                                              20

<210> SEQ ID NO 36
<211> LENGTH: 20
<212> TYPE: DNA
<213> ORGANISM: HIV

<400> SEQUENCE: 36
aaaactcttg ccttatggcc                                              20

<210> SEQ ID NO 37
<211> LENGTH: 20
<212> TYPE: DNA
<213> ORGANISM: HIV

<400> SEQUENCE: 37
tacttggctc attgcttcag                                              20

<210> SEQ ID NO 38
<211> LENGTH: 20
<212> TYPE: DNA
<213> ORGANISM: HIV

<400> SEQUENCE: 38
ctgcatcatt atggtagctg                                              20

<210> SEQ ID NO 39
<211> LENGTH: 20
<212> TYPE: DNA
<213> ORGANISM: HIV

<400> SEQUENCE: 39
ctttggttcc taaaattgcc                                              20

<210> SEQ ID NO 40
<211> LENGTH: 20
```

<212> TYPE: DNA
<213> ORGANISM: HIV

<400> SEQUENCE: 40
cccttctttg ccacaattga                                           20

<210> SEQ ID NO 41
<211> LENGTH: 20
<212> TYPE: DNA
<213> ORGANISM: HIV

<400> SEQUENCE: 41
tccaacagcc cttttttccta                                          20

<210> SEQ ID NO 42
<211> LENGTH: 20
<212> TYPE: DNA
<213> ORGANISM: HIV

<400> SEQUENCE: 42
tttggtgtcc ttcctttcca                                           20

<210> SEQ ID NO 43
<211> LENGTH: 20
<212> TYPE: DNA
<213> ORGANISM: HIV

<400> SEQUENCE: 43
cctgtctctc agtacaatct                                           20

<210> SEQ ID NO 44
<211> LENGTH: 20
<212> TYPE: DNA
<213> ORGANISM: HIV

<400> SEQUENCE: 44
ggccagatct tccctaaaaa                                           20

<210> SEQ ID NO 45
<211> LENGTH: 20
<212> TYPE: DNA
<213> ORGANISM: HIV

<400> SEQUENCE: 45
aagaaaattc cctggccttc                                           20

<210> SEQ ID NO 46
<211> LENGTH: 20
<212> TYPE: DNA
<213> ORGANISM: HIV

<400> SEQUENCE: 46
acctgaagct ctcttctggt                                           20

<210> SEQ ID NO 47
<211> LENGTH: 20
<212> TYPE: DNA
<213> ORGANISM: HIV

<400> SEQUENCE: 47
tacagttcct tgtctatcgg                                           20

<210> SEQ ID NO 48

-continued

```
<211> LENGTH: 20
<212> TYPE: DNA
<213> ORGANISM: HIV

<400> SEQUENCE: 48
tgacctgagg gaagttaaag                                               20

<210> SEQ ID NO 49
<211> LENGTH: 20
<212> TYPE: DNA
<213> ORGANISM: HIV

<400> SEQUENCE: 49
ccacaatttt tctgtagcac                                               20

<210> SEQ ID NO 50
<211> LENGTH: 20
<212> TYPE: DNA
<213> ORGANISM: HIV

<400> SEQUENCE: 50
gtaccccata atagactgtg                                               20

<210> SEQ ID NO 51
<211> LENGTH: 20
<212> TYPE: DNA
<213> ORGANISM: HIV

<400> SEQUENCE: 51
aatagagtgg tggttgcttc                                               20

<210> SEQ ID NO 52
<211> LENGTH: 20
<212> TYPE: DNA
<213> ORGANISM: HIV

<400> SEQUENCE: 52
tgctttagca tctgatgcac                                               20

<210> SEQ ID NO 53
<211> LENGTH: 20
<212> TYPE: DNA
<213> ORGANISM: HIV

<400> SEQUENCE: 53
gcccaaacat tatgtacctc                                               20

<210> SEQ ID NO 54
<211> LENGTH: 20
<212> TYPE: DNA
<213> ORGANISM: HIV

<400> SEQUENCE: 54
tgtgggtaca caggcatgtg                                               20

<210> SEQ ID NO 55
<211> LENGTH: 20
<212> TYPE: DNA
<213> ORGANISM: HIV

<400> SEQUENCE: 55
tactacttct tgtgggttgg                                               20
```

```
<210> SEQ ID NO 56
<211> LENGTH: 20
<212> TYPE: DNA
<213> ORGANISM: HIV

<400> SEQUENCE: 56
ccatgtcatt tttccacatg                                               20

<210> SEQ ID NO 57
<211> LENGTH: 20
<212> TYPE: DNA
<213> ORGANISM: HIV

<400> SEQUENCE: 57
atatcctcat gcatctgttc                                               20

<210> SEQ ID NO 58
<211> LENGTH: 20
<212> TYPE: DNA
<213> ORGANISM: HIV

<400> SEQUENCE: 58
ggctttgatc ccataaactg                                               20

<210> SEQ ID NO 59
<211> LENGTH: 20
<212> TYPE: DNA
<213> ORGANISM: HIV

<400> SEQUENCE: 59
ctaacacaga gtggggttaa                                               20

<210> SEQ ID NO 60
<211> LENGTH: 20
<212> TYPE: DNA
<213> ORGANISM: HIV

<400> SEQUENCE: 60
cattcttcaa atcagtgcac                                               20

<210> SEQ ID NO 61
<211> LENGTH: 20
<212> TYPE: DNA
<213> ORGANISM: HIV

<400> SEQUENCE: 61
cccgctacta ctattggtat                                               20

<210> SEQ ID NO 62
<211> LENGTH: 20
<212> TYPE: DNA
<213> ORGANISM: HIV

<400> SEQUENCE: 62
ctctcctttc tccattatca                                               20

<210> SEQ ID NO 63
<211> LENGTH: 20
<212> TYPE: DNA
<213> ORGANISM: HIV

<400> SEQUENCE: 63
gctgatattg aaagagcagt                                               20
```

-continued

```
<210> SEQ ID NO 64
<211> LENGTH: 20
<212> TYPE: DNA
<213> ORGANISM: HIV

<400> SEQUENCE: 64
gcaccttacc tcttatgctt                                              20

<210> SEQ ID NO 65
<211> LENGTH: 20
<212> TYPE: DNA
<213> ORGANISM: HIV

<400> SEQUENCE: 65
gtcaacttat agctggtagt                                              20

<210> SEQ ID NO 66
<211> LENGTH: 20
<212> TYPE: DNA
<213> ORGANISM: HIV

<400> SEQUENCE: 66
ctgtgtaatg actgaggtgt                                              20

<210> SEQ ID NO 67
<211> LENGTH: 20
<212> TYPE: DNA
<213> ORGANISM: HIV

<400> SEQUENCE: 67
caaaggatac ctttggacag                                              20

<210> SEQ ID NO 68
<211> LENGTH: 20
<212> TYPE: DNA
<213> ORGANISM: HIV

<400> SEQUENCE: 68
ggcacaataa tgtatgggaa                                              20

<210> SEQ ID NO 69
<211> LENGTH: 20
<212> TYPE: DNA
<213> ORGANISM: HIV

<400> SEQUENCE: 69
ttagaatcgc aaaaccagcc                                              20

<210> SEQ ID NO 70
<211> LENGTH: 20
<212> TYPE: DNA
<213> ORGANISM: HIV

<400> SEQUENCE: 70
cctgttccat tgaacgtctt                                              20

<210> SEQ ID NO 71
<211> LENGTH: 20
<212> TYPE: DNA
<213> ORGANISM: HIV

<400> SEQUENCE: 71
gtacattgta ctgtgctgac                                              20
```

<210> SEQ ID NO 72
<211> LENGTH: 20
<212> TYPE: DNA
<213> ORGANISM: HIV

<400> SEQUENCE: 72
gatactactg gcctaattcc                                                 20

<210> SEQ ID NO 73
<211> LENGTH: 20
<212> TYPE: DNA
<213> ORGANISM: HIV

<400> SEQUENCE: 73
gccatttaac agcagttgag                                                 20

<210> SEQ ID NO 74
<211> LENGTH: 20
<212> TYPE: DNA
<213> ORGANISM: HIV

<400> SEQUENCE: 74
ctacctcttc ttctgctaga                                                 20

<210> SEQ ID NO 75
<211> LENGTH: 20
<212> TYPE: DNA
<213> ORGANISM: HIV

<400> SEQUENCE: 75
gtccgtgaaa ttgacagatc                                                 20

<210> SEQ ID NO 76
<211> LENGTH: 20
<212> TYPE: DNA
<213> ORGANISM: HIV

<400> SEQUENCE: 76
cagatgtgtt cagctgtact                                                 20

<210> SEQ ID NO 77
<211> LENGTH: 20
<212> TYPE: DNA
<213> ORGANISM: HIV

<400> SEQUENCE: 77
gttgttgggt cttgtacaat                                                 20

<210> SEQ ID NO 78
<211> LENGTH: 20
<212> TYPE: DNA
<213> ORGANISM: HIV

<400> SEQUENCE: 78
ctctctggat acggattctt                                                 20

<210> SEQ ID NO 79
<211> LENGTH: 20
<212> TYPE: DNA
<213> ORGANISM: HIV

<400> SEQUENCE: 79

-continued tgtaacaaat gctctccctg                    20

<210> SEQ ID NO 80
<211> LENGTH: 20
<212> TYPE: DNA
<213> ORGANISM: HIV

<400> SEQUENCE: 80
gtgcttgtct catatttcct                    20

<210> SEQ ID NO 81
<211> LENGTH: 20
<212> TYPE: DNA
<213> ORGANISM: HIV

<400> SEQUENCE: 81
ccatttTgct ctactaatgt                    20

<210> SEQ ID NO 82
<211> LENGTH: 20
<212> TYPE: DNA
<213> ORGANISM: HIV

<400> SEQUENCE: 82
gctagctatc tgttttaaag                    20

<210> SEQ ID NO 83
<211> LENGTH: 20
<212> TYPE: DNA
<213> ORGANISM: HIV

<400> SEQUENCE: 83
ctcctgagga ttgcttaaag                    20

<210> SEQ ID NO 84
<211> LENGTH: 20
<212> TYPE: DNA
<213> ORGANISM: HIV

<400> SEQUENCE: 84
tgcgttacaa tttctgggtc                    20

<210> SEQ ID NO 85
<211> LENGTH: 20
<212> TYPE: DNA
<213> ORGANISM: HIV

<400> SEQUENCE: 85
gtagaaaaat tcccctccac                    20

<210> SEQ ID NO 86
<211> LENGTH: 20
<212> TYPE: DNA
<213> ORGANISM: HIV

<400> SEQUENCE: 86
ccttcagtac tccaagtact                    20

<210> SEQ ID NO 87
<211> LENGTH: 20
<212> TYPE: DNA
<213> ORGANISM: HIV

<400> SEQUENCE: 87

```
gtgtcacttc cttcagtgtt                                              20

<210> SEQ ID NO 88
<211> LENGTH: 20
<212> TYPE: DNA
<213> ORGANISM: HIV

<400> SEQUENCE: 88
tttattctgc atgggagggt                                              20

<210> SEQ ID NO 89
<211> LENGTH: 20
<212> TYPE: DNA
<213> ORGANISM: HIV

<400> SEQUENCE: 89
cctactttct gccacatgtt                                              20

<210> SEQ ID NO 90
<211> LENGTH: 20
<212> TYPE: DNA
<213> ORGANISM: HIV

<400> SEQUENCE: 90
aatttgtcca ctgatgggag                                              20

<210> SEQ ID NO 91
<211> LENGTH: 20
<212> TYPE: DNA
<213> ORGANISM: HIV

<400> SEQUENCE: 91
cagccctgta atatttgatg                                              20

<210> SEQ ID NO 92
<211> LENGTH: 20
<212> TYPE: DNA
<213> ORGANISM: HIV

<400> SEQUENCE: 92
gctattacca ccatctcttg                                              20

<210> SEQ ID NO 93
<211> LENGTH: 20
<212> TYPE: DNA
<213> ORGANISM: HIV

<400> SEQUENCE: 93
tgaagatctc ggactcattg                                              20

<210> SEQ ID NO 94
<211> LENGTH: 20
<212> TYPE: DNA
<213> ORGANISM: HIV

<400> SEQUENCE: 94
attgtccctc atatctcctc                                              20

<210> SEQ ID NO 95
<211> LENGTH: 20
<212> TYPE: DNA
<213> ORGANISM: HIV
```

```
<400> SEQUENCE: 95
gtgctactcc taatggttca                                             20

<210> SEQ ID NO 96
<211> LENGTH: 20
<212> TYPE: DNA
<213> ORGANISM: HIV

<400> SEQUENCE: 96
actcttctct ttgccttggt                                             20
```